United States Patent
Nguyen et al.

(10) Patent No.: US 10,265,551 B2
(45) Date of Patent: *Apr. 23, 2019

(54) USE OF A COMPOSITION AND PROCESS INVOLVING THE USE OF A NON-HYDROXIDE BASE AND A PROTEIN DENATURANT WITH HEAT FOR RELAXING OR STRAIGHTENING HAIR

(75) Inventors: Nghi Van Nguyen, Edison, NJ (US); Katherine Natalie Barger, Mooresville, NC (US); Cynthia Chong Espino, Princeton, NJ (US); David W. Cannell, New Hope, PA (US)

(73) Assignee: L'OREAL, Paris (FR)

( * ) Notice: Subject to any disclaimer, the term of this patent is extended or adjusted under 35 U.S.C. 154(b) by 1032 days.

This patent is subject to a terminal disclaimer.

(21) Appl. No.: 12/864,294

(22) PCT Filed: Mar. 16, 2009

(86) PCT No.: PCT/US2009/037245
§ 371 (c)(1),
(2), (4) Date: Sep. 20, 2010

(87) PCT Pub. No.: WO2009/117344
PCT Pub. Date: Sep. 24, 2009

(65) Prior Publication Data
US 2011/0052520 A1    Mar. 3, 2011

Related U.S. Application Data

(60) Provisional application No. 61/037,862, filed on Mar. 19, 2008.

(51) Int. Cl.
*A61Q 5/04* (2006.01)
*A61K 8/41* (2006.01)
*A61K 8/42* (2006.01)
*A61K 8/44* (2006.01)

(52) U.S. Cl.
CPC ............ *A61Q 5/04* (2013.01); *A61K 8/41* (2013.01); *A61K 8/42* (2013.01); *A61K 8/44* (2013.01)

(58) Field of Classification Search
None
See application file for complete search history.

(56) References Cited

U.S. PATENT DOCUMENTS

| | | |
|---|---|---|
| 2,437,965 A | 3/1948 | Michaels et al. |
| 2,770,599 A | 11/1956 | Henkin |
| 3,457,027 A | 7/1969 | Bolinger et al. |
| 3,973,574 A | 8/1976 | Minagawa et al. |
| 4,228,810 A | 10/1980 | Moore et al. |
| 4,296,764 A | 10/1981 | Pallone et al. |
| 4,524,787 A | 6/1985 | Khalil et al. |
| 4,793,994 A | 12/1988 | Helioff et al. |
| 4,847,076 A | 7/1989 | Deshpande et al. |
| 5,520,209 A | 5/1996 | Goins et al. |
| 5,520,909 A | 5/1996 | Salce et al. |
| 5,565,216 A | 10/1996 | Cowsar et al. |
| 5,776,443 A | 7/1998 | Vinski et al. |
| 5,833,966 A | 11/1998 | Samain |
| 5,854,319 A | 12/1998 | O'Lenick, Jr. et al. |
| 6,491,902 B2 | 12/2002 | Shefer et al. |
| 6,706,674 B2 | 3/2004 | Cincotta et al. |
| 6,805,136 B2 | 10/2004 | Browning |
| 7,638,117 B2 | 12/2009 | Shami |
| 2001/0023235 A1 | 9/2001 | Crudele et al. |
| 2002/0110583 A1 | 8/2002 | Grey |
| 2002/0146379 A1 | 10/2002 | Shefer et al. |
| 2002/0155962 A1 | 10/2002 | Cincotta et al. |
| 2004/0034946 A1 | 2/2004 | Legrand et al. |
| 2004/0122105 A1 | 6/2004 | Bettle et al. |
| 2004/0146476 A1 | 7/2004 | Shami |
| 2005/0048018 A1 | 3/2005 | Fadeeva et al. |
| 2005/0136016 A1 | 6/2005 | Malle et al. |
| 2005/0136017 A1* | 6/2005 | Malle et al. ............... 424/70.2 |

(Continued)

FOREIGN PATENT DOCUMENTS

| | | |
|---|---|---|
| DE | 19855606 A1 | 6/2000 |
| EP | 0640643 A2 | 3/1995 |

(Continued)

OTHER PUBLICATIONS

International Search Report and Written Opinion dated Apr. 20, 2009 as received in corresponding PCT application No. PCT/US2009/037245.
International Preliminary Report on Patentability dated Sep. 30, 2010 as received in corresponding PCT application No. PCT/US2009/037245.
U.S. Appl. No. 12/864,294, Present application—not published yet—listed for information, Nguyen et al.
U.S. Appl. No. 11/717,824, filed Sep. 18, 2008, US-2008-0223392, Cannell et al.
U.S. Appl. No. 11/446,718, filed Dec. 6, 2007, US-2007-0280896, Nguyen et al.

(Continued)

*Primary Examiner* — Jyothsna A Venkat
(74) *Attorney, Agent, or Firm* — Polsinelli PC

(57) ABSTRACT

A process for straightening or relaxing hair involving the steps of: (a) providing a hair straightening/relaxing composition containing: (i) from about 0.1 to about 50% by weight of at least one non-hydroxide base; (ii) from about greater than 0% to about 50% of at least one protein denaturant; and (iii) remainder, to 100%, a cosmetically acceptable medium, all weights based on the weight of the hair straightening/relaxing composition; (b) contacting the hair with the hair straightening/relaxing composition to form treated hair; (c) optionally, rinsing the hair straightening/relaxing composition from the treated hair; (d) optionally, contacting the treated hair with a non-volatile oil; and (e) smoothing the treated hair using a combination of heat and means for physically smoothing hair.

16 Claims, No Drawings

(56) References Cited

U.S. PATENT DOCUMENTS

| | | | |
|---|---|---|---|
| 2005/0136018 A1 | 6/2005 | Malle et al. | |
| 2005/0186232 A1 | 8/2005 | Malle et al. | |
| 2006/0127337 A1* | 6/2006 | Radisson | 424/70.2 |
| 2006/0228316 A1 | 10/2006 | Cannell et al. | |
| 2006/0251599 A1* | 11/2006 | Savaides et al. | 424/70.5 |
| 2007/0280895 A1 | 12/2007 | Nguyen et al. | |
| 2011/0052520 A1 | 3/2011 | Nguyen et al. | |
| 2012/0132224 A1 | 5/2012 | Nguyen et al. | |

FOREIGN PATENT DOCUMENTS

| | | |
|---|---|---|
| EP | 1532963 A1 | 5/2005 |
| EP | 1532964 A1 | 5/2005 |
| FR | 2862212 A1 | 5/2005 |
| FR | 2862213 A1 | 5/2005 |
| GB | 1416565 A | 12/1975 |
| GB | 1545297 A | 5/1979 |
| GB | 1600807 A | 10/1981 |
| JP | H03251519 A | 11/1991 |
| JP | H05331029 A | 12/1993 |
| JP | H06192051 A | 7/1994 |
| JP | H09132515 A | 5/1997 |
| JP | 2000256146 A | 9/2000 |
| JP | 2000302647 A | 10/2000 |
| JP | 2002138022 A | 5/2002 |
| JP | 2002308725 A | 10/2002 |
| JP | 2003171238 A | 6/2003 |
| JP | 2004026770 * | 1/2004 |
| JP | 2008222717 A | 9/2008 |
| WO | 2009117344 A2 | 9/2009 |

OTHER PUBLICATIONS

U.S. Appl. No. 11/378,152, filed Sep. 20, 2007, US-2007-0218027, Nguyen et al.

Chinese Office Action for Application No. 200780020658.7 dated Sep. 29, 2013.

Flat Ironing Creme. http://web.archive.org/web/20060103033615/http://www.growafrohairlong.com/flatironing.html, Accessed Apr. 14, 2010, Archived Jan. 3, 2006.

Glossary of Cosmetics Terms. http://www.salonweb.com/pro/glossary.htm. Published Nov. 8, 2001.

Golczewski. Exp Gerontal. 1984; 19( 1 ): Abstract only.

How Long Do You Process. http://www.longhaircareforum.com/showthread.php?t=91703. Published Jun. 29, 2006.

International Preliminary Report on Patentability dated Dec. 10, 2008 in corresponding PCT application No. PCT/US07/09645.

International Search Report and Written Opinion of the International Searching Authority dated Aug. 11, 2008 in corresponding PCT application No. PCT/US07/09645.

International Search Report for Application PCTUS07/09645 dated Aug. 11, 2008.

Japanese Straightening FAQ. http://straightening.blogspot.com/2005_05_01 archive.html Accessed Apr. 13, 2010.

Jerry March, Advanced Organic Chemistry, Reactions, Mechanisms, and Structure, Third Edition, pp. 218 to 223, A Wiley-Interscience Publication, John Wiley&Sons, New York, Chichester, Brisbane, Toronto, Singapore, Copyright 1985.

Milady's Standard Cosmetology. Copyright 2004. Milady.

Office Action from Chinese Application No. 200780020658.7, dated Jun. 10, 2010.

Office Action from Chinese Application No. 200780020658.7, dated Mar. 2, 2011.

Perm Can Hurt or Help. http://www.naturallycurly.com/curlreading/straightening/perm-can-hurt-or-help. Accessed Apr. 13, 2010.

Production Chemicals for the Oil and Gas Industry. Copyright 2009. Malcom A Kelland.

Solano Professional Flat Iron as accessed from http://www.health-store.com/hairtools.html on Apr. 6, 2009 as archived Jun. 2, 2002.

* cited by examiner

USE OF A COMPOSITION AND PROCESS INVOLVING THE USE OF A NON-HYDROXIDE BASE AND A PROTEIN DENATURANT WITH HEAT FOR RELAXING OR STRAIGHTENING HAIR

CROSS-REFERENCE TO RELATED APPLICATION

This application is a national phase of PCT/US2009/037245, filed Mar. 16, 2009, which claims priority to U.S. Provisional Application No. 61/037,862, filed Mar. 19, 2008, the contents of which are incorporated by reference.

BACKGROUND OF THE INVENTION

Hair straightening or hair relaxing products have been commercially available for over fifty years for people who want straighter, more manageable hair. Most commercially available hair relaxers are composed of a strong hydroxide base that breaks the bonds in the hair.

Commercial products based only on alkaline metal hydroxides such as sodium hydroxide and lithium hydroxide are typically used to straighten or relax curly/kinky hair. There are primarily four different types of alkaline metal hydroxide hair straighteners in use: calcium hydroxide, lithium hydroxide, sodium hydroxide, and potassium hydroxide. The straightening product is usually applied quickly and can only remain in the hair for a very limited amount of time. Due to the alkalinity of such products, if the product is not rinsed from the hair at the appropriate time, damage to the hair can occur, as well as chemical burns to the scalp and areas surrounding the hair.

Other relaxing formulations use guanidinium hydroxide which can be formed from the reaction of guanidine carbonate and a very small amount of soluble hydroxide such as calcium hydroxide. The reaction between these two compounds leads to the formation of guanidinium hydroxide and calcium carbonate, which precipitates in the composition. The presence of this precipitate makes the final rinsing of the hair much more difficult and leaves on the hair and the scalp mineral particles that give it a coarse feel and an unattractive appearance resembling dandruff, although such a system may provide a better relaxing efficacy and better skin tolerance. However, these technologies using hydroxide bases are very aggressive for the hair and the scalp and require very strict control of the application time to avoid excessive irritation and impairment of the hair, which may go as far as breaking of the hair.

Other hair relaxing or straightening systems may involve the use of protein denaturants in combination with heat in the absence of hydroxide or non-hydroxide bases. Protein denaturants are compounds which cause a reversible unfolding of a protein.

Thus, the object of the present invention is to provide a hair straightening or relaxing process which is safer than, yet more effective as, conventional processes. It was surprisingly discovered that the use of such a process involving the use of at least one non-hydroxide base, at least one protein denaturant, and a combination of heat and means for physically smoothing hair resulted in significantly better straightening efficiency.

BRIEF SUMMARY OF THE INVENTION

The present invention is directed to a process for straightening or relaxing hair involving the steps of:

(a) providing a hair straightening/relaxing composition containing:
  (i) from about 0.1 to about 50% by weight of at least one non-hydroxide base;
  (ii) from about greater than 0% to about 50% of at least one protein denaturant;
  (iii) remainder, to 100%, a cosmetically acceptable medium, all weights based on the weight of the hair straightening/relaxing composition;
(b) contacting the hair with the hair straightening/relaxing composition to form treated hair;
(c) optionally, rinsing the hair straightening/relaxing composition from the treated hair;
(d) optionally, contacting the treated hair with a non-volatile oil; and
(e) smoothing the treated hair using a combination of heat and means for physically smoothing hair.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

It has been surprisingly found that by employing the process of the present invention, straightening/relaxing of hair can be achieved in a manner which is less harmful to a user's skin and hair than conventional hair straightening/relaxing processes.

Conventional products, which employ large amounts of hydroxide, have a tendency to cause skin irritation, as well as damage to the hair itself, due to the use of large amounts of hydroxide in said products. However, by using a product containing a non-hydroxide base, a protein denaturant, and then smoothing the hair by employing a combination of heat and means for physically smoothing the hair, satisfactory straightening/relaxing of the hair can be achieved in a manner that is less harmful to both skin and hair.

Suitable non-hydroxide bases for use in the present invention are those bases having a pKa of from about 0 to about 15, preferably from about 1 to about 14, and more preferably from about 2 to about 13. These may be chosen from organic bases and inorganic bases.

Organic bases generally include nitrogen-containing bases which do not completely disassociate in water. Examples thereof include, but are not limited to, ethylamines, ethyleneamines, ethanolamines, quinoline, aniline, pyridine, basic amino acids, and their derivatives.

Particularly preferred nitrogen-containing bases include ethylenediamines, monoethanolamines, arginine, lysine, and their derivatives, and mixtures thereof.

Inorganic bases generally include alkali metal phosphates and carbonates such as, for example, sodium phosphate, potassium phosphate, sodium carbonate, sodium bicarbonate, potassium carbonate, potassium bicarbonate, and their derivatives.

Inorganic bases may also include alkali metals of carboxylates such as, for example, sodium acetate, potassium acetate, sodium citrate, and potassium citrate, and their derivatives.

Particularly preferred inorganic bases include potassium phosphate, sodium phosphate, and sodium carbonate.

The non-hydroxide base is typically employed in the hair straightening/relaxing composition in an amount of from about 0.1% to about 50% by weight, preferably from about 0.1% to about 30% by weight, preferably from about 0.1% to about 10% by weight, based on the total weight of the composition.

Suitable protein denaturants for use in the present invention can be chosen from ureas, guanidines, amidines, urethanes, aromatic monohydroxylated, dihydroxylated, trihydroxylated or polyhydroxylated derivatives, nitrogen heterocycles of the imidazole or triazole family, carboxylic acids and amide and thioamide derivatives thereof, thioureas, amino acids, alcohols, polyols, amine oxides, surfactants containing sugar, choline, deoxycholine or polyethylene glycol units, metal salts and sulfamides.

As "urea" that may be used as relaxing active agent, this term refers to any derivative comprising in its chemical formula a carbonyl group simply bonded to 2 nitrogen atoms. These ureas are more particularly selected from the compounds of general formulae (I) and (II) below:

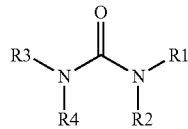

(I)

in which:

R1, R2, R3 and R4 represent, independently:

(i) a hydrogen atom, or (ii) a linear or branched lower C1-C4 alkyl or alkenyl radical, optionally substituted with a radical chosen from: hydroxyl, amino, dimethylamino, carboxyl or carboxamide or N-methylcarboxamide.

When R1, R2 and R3 represent a hydrogen atom, R4 may also denote a radical chosen from the following: carboxamide; methoxy; ethoxy; 1,2,4-triazolyl; cyclopentyl; methoxycarbonyl; ethoxycarbonyl; CO—CH=CH—COOH; phenyl optionally substituted with a chlorine atom or a hydroxyl radical; benzyl; or 2,5-dioxo-4-imidazolidinyl.

When R1 and R3 represent a hydrogen atom, R2 may also represent a hydrogen atom or a methyl or ethyl radical and R4 an acetyl radical.

When R1=R2=H, R3 and R4 may also form, with the nitrogen atom that bears them, a piperidine or 3-methylpyrazole or 3,5-dimethylpyrazole or maleimide ring.

Finally, R1 and R2, and also R3 and R4, may also form, with the nitrogen atom that bears them, an imidazole ring.

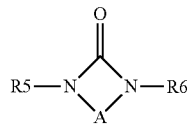

(II)

in which:

R5 and R6 represent, independently of each other:

(i) a hydrogen atom, or (ii) a linear or branched C1-C4 lower alkyl radical, optionally substituted with a radical chosen from: hydroxyl, amino, dimethylamino, carboxyl or carboxamide.

and A represents the radicals: CH2-CH2 or CH=CH or CH2-CO or CO—NH or CH=N or CO—CO or CHOH—CHOH or (HOOC)CH—CH or CHOH—CO or CH2-CH2-CH2 or CH2-NH—CO or CH=C(CH3)—CO or NH—CO—NH or CH2-CH2-CO or CH2-N(CH3)—CH2 or NH—CH2-NH or CO—CH(CH3)—CH2 or CO—CH2-CO or CO—NH—CO or CO—CH(COOH)—CH2 or CO—CH=C(COOH) or CO—CH=C(CH3) or CO—C(NH2)=CH or CO—C(CH3)=N or CO—CH=CH or CO—CH=N or CO—N=CH.

As "guanidine" that may be used as relaxing active agent, this term means any derivative comprising in its chemical formula at least one carbon atom doubly bonded to a nitrogen atom and singly bonded to two other nitrogen atoms. These guanidines are more particularly selected from the compounds of general formula (III) below:

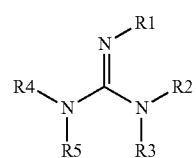

(III)

in which:

R1, R2, R3, R4 and R5 represent, independently:

(iii) a hydrogen atom, or (iv) a linear or branched C1-C4 lower alkyl or alkenyl radical, optionally substituted with one or two radicals chosen from: hydroxyl, amino, dimethylamino, methoxy, ethoxy, carboxyl, carboxamide, N-methylcarboxamide or SO3H When R1, R2, R3 and R4 represent a hydrogen atom, R5 may also denote a radical chosen from the following: acetyl; chloroacetyl; carboxamide; methoxy; ethoxy; 1,2,4-triazolyl; cyclopentyl; methoxycarbonyl; ethoxycarbonyl; CO—CH=CH—COOH; phenyl optionally substituted with a chlorine atom or a hydroxyl radical; benzyl; thiazolidone; benzimidazole; benzoxazole; benzothiazole; or C(=NH)—NR6R7 in which R6 and R7 denote, independently of each other, a hydrogen atom or a linear or branched C1-C4 lower alkyl radical, optionally substituted with one or two radicals chosen from: hydroxyl, amino, dimethylamino, carboxyl and carboxamide; or N-methylcarboxamide; or alternatively a phenyl radical.

When R1=R2=R3=H, R4 and R5 may also form, with the nitrogen atom that bears them, a pyrrolidine, piperidine, pyrazole or 1,2,4-triazole ring, optionally substituted with one or two radicals chosen from: hydroxyl, amino and carboxyl.

When R1=R2=H, and R4=H or methyl, R3 and R5 may also together form a 5-membered ring optionally containing an oxo group, and the organic or mineral salts thereof.

The protein denaturant is preferably a urea or a guanidine, urea derivatives and/or salts, guanidine derivatives and/or salts, arginine, other compounds and their salts containing a guanidine moiety, and mixtures thereof.

Some of the protein denaturants may also fit the description of the non-hydroxide base and therefore, can be used as the non-hydroxide base according to the invention.

As used herein, the term "cosmetically acceptable medium" is known to one of ordinary skill in the art, and may comprise, for example, water and/or at least one organic solvent.

The hair straightening/relaxing composition disclosed herein may be, for example, in the form of a thickened cream so as to hold the hair as stiff as possible. These creams are made in the form of "heavy" emulsions, for example, based on glyceryl stearate, glycol stearate, self-emulsifying waxes, fatty alcohols, mineral oil and petrolatum.

Liquids or gels containing thickeners, such as carboxyvinyl polymers or copolymers that "stick" the hairs together and hold them in a smooth position during the leave-in time, may also be used.

The hair straightening/relaxing composition as disclosed herein may also comprise at least one adjuvant chosen, for example, from silicones in soluble, dispersed and microdispersed forms, nonionic, anionic, cationic and amphoteric surfactants, ceramides, glycoceramides and pseudoceramides, vitamins and provitamins including panthenol, waxes other than ceramides, glycoceramides and pseudoceramides, water-soluble and liposoluble, silicone-based and non-silicone-based sunscreens, nacreous agents and opacifiers, sequestering agents, plasticizers, solubilizers, acidifying agents, mineral and organic thickeners, antioxidants, hydroxy acids, penetrating agents, fragrances, and preserving agents.

In the event that surfactants are employed in the composition of the present invention, said composition may be used as a shampoo. Similarly, in the event that one were to decide to use the composition of the invention as a hair conditioner, various types of conditioning agents can be added to the composition in order to facilitate this hair treating property.

Smoothing of hair treated with the above-disclosed hair straightening/relaxing composition involves using a combination of heat and means for physically smoothing the hair. The heat necessary to effectuate smoothing should be at least 50° C.; preferably at least 75° C.; preferably at least 100° C. The precise amount of heat employed will depend on the concentration of the non-hydroxide compound present in the composition. This heat may emanate from any suitable source such as, for example, a hair dryer or hot/flat iron.

The means for physically smoothing hair can be any apparatus capable of physically smoothing the hair such as, for example, a hair brush or comb. In one embodiment, the means for smoothing hair also serves as the source for generating heat such as, for example, a hot/flat iron.

A pre-alkalizing step may also be used before the application of the inventive composition. This renders the hair straightening/relaxing process more efficient and less time-consuming.

The alkaline composition may be employed in any suitable form. Examples thereof include, but are not limited to, a shampoo, a conditioner or an alkaline solution in general. In a particularly preferred embodiment, the alkaline composition is in the form of a shampoo which would facilitate both the pre-alkalizing and cleaning of the hair at the same time.

According to one embodiment of the present invention, there is provided a process for straightening or relaxing hair involving the steps of: (a) contacting the hair with the above-disclosed hair straightening/relaxing composition to form treated hair; (b) optionally, rinsing the hair straightening/relaxing composition from the treated hair, after it has been in contact with the hair for a period of less than 60 minutes, preferably less than 40 minutes, preferably less than 30 minutes, preferably less than 20 minutes; (c) optionally, contacting the treated hair with a non-volatile oil chosen from plant, animal, mineral and synthetic oils; and (d) smoothing the treated hair using a combination of heat and means for physically smoothing hair.

As is disclosed above, the hair straightening/relaxing composition may either be left on the hair, or rinsed out. As for the non-volatile oil, if employed, it will preferably remain on the hair.

According to another embodiment of the present invention, there is provided a process for straightening or relaxing hair involving the steps of: (a) optionally, contacting the hair with a non-volatile oil chosen from plant, animal, mineral and synthetic oils; (b) smoothing the treated hair using a combination of heat and means for physically smoothing hair to form smoothed hair; (c) contacting the smoothed hair with the hair straightening/relaxing composition to form treated hair; (d) optionally, rinsing the hair straightening/relaxing composition from the treated hair after it has been in contact with the hair for a period of less than 60 minutes, preferably less than 40 minutes, preferably less than 30 minutes, preferably less than 20 minutes; and (e) optionally, smoothing the treated hair using a combination of heat and means for physically smoothing hair to form smoothed hair.

It should be noted that the steps of: contacting the hair with a non-volatile oil; and smoothing the hair, may be performed prior to and/or after application of the hair straightening/relaxing composition.

In commercially available hair straightening or relaxing compositions, the highly caustic hydroxide compound such as sodium hydroxide must be used in order to satisfactorily straighten/relax the hair without heat. In the present invention, however, the less caustic and the lower concentrations of the non-hydroxide compound can be used because of the synergy realized by using a combination of heat and an apparatus capable of physically smoothing the hair. Without intending to be bound by theory, it is believed that a synergistic effect in hair straightening/relaxing is realized due to an induced supercontraction and denaturation of hair protein caused by the combination of heat and physical smoothing.

Moreover, due to the less caustic and the lower concentrations of the non-hydroxide compound being used, a barrier substance is not required when using the hair straightening/relaxing composition of the present invention. Commercially available hair relaxing products oftentimes require the hair stylist to apply a barrier substance such as petrolatum to the skin surrounding the scalp and the area around the ears. The barrier substance is used to prevent the skin from becoming irritated if the hair relaxing product contacts the skin. A barrier substance is not necessary when using the process of the present invention because the concentration and the irritation of the non-hydroxide compound is much lower.

The present invention will be better understood from the examples which follow, all of which are intended for illustrative purposes only, and are not meant to unduly limit the scope of the invention in any way.

EXAMPLES

General Procedure to Test the Straightening Efficiency of the Kinky Hair

The tests were done on hair swatches made of 30 strands of kinky hair, 8 cm long (full length when straight). The following treatments were performed:

The hair swatches were shampooed with an alkaline shampoo (11.5% ALS, 3.5% Cocamidopropyl Hydroxysultaine, pH 8.8) two times. The shampooed hair swatch was then soaked in the test solution (inventive composition) for 20 minutes. The treated hair swatch was blotted dry, placed in a humidity chamber (80% RH) for 30 minutes and straightened by passing a flat iron (400° F.) through the hair 3 times (5 seconds/pass). After equilibration at ambient condition for 5 minutes, the straightened hair was shampooed (15% SLES, pH 6.0) and allowed to air dry. The straightening efficiency (% SE) is calculated using the following formula:

% SE=(Lf−Li)/(Ls−Li)×100

Where: Lf=Final length (after air dry)
Li=Initial length (before ironing)
Ls=Straight length (8 cm)

Example 1. Synergistic Effect of Base and Protein Denaturant

Following the General Procedure, the straightening efficiency of the present invention containing the base and the protein denaturant (q.s. to 100% with water) was measured. The synergistic effect of the base and the protein denaturant in hair straightening is shown in Table 1:

TABLE 1

| Testing Solution | % SE |
|---|---|
| 1% MEA | 10.6 |
| 1% Guanidine Hydrochloride | 36.2 |
| 1% MEA + 1% Guanidine Hydrochloride | 69.2 |
| 1% MEA | 9.6 |
| 10% Urea | 15.2 |
| 1% MEA + 10% Urea | 76.7 |

Example 2. Straightening Efficiency of Various Testing Solutions

Following the General Procedure, the straightening efficiency of the present invention containing various bases and the protein denaturants (q.s. to 100% with water) was measured. The results are shown in Table 2:

TABLE 2

| Testing Solution | | |
|---|---|---|
| Base | Protein Denaturant | % SE |
| 1% MEA | 3% Guanidine•HCl | 93.0 |
| 1% MEA | 2% Diamino-Guanidine•HCl | 89.4 |
| 1% MEA | 15% Urea | 81.4 |
| 1% MEA | 3% Aminoguanidine•HCl | 93.1 |
| 10% Lysine | 5% Guanidine•HCl | 76.4 |
| 5% Arginine | 10% Guanidine•HCl | 90.3 |

The results from the two examples above show that the hair straightening efficiency was significantly greater when using the process consisting of the inventive compositions and application of heat compared to the process consisting of compositions that contain only the non-hydroxide base and application of heat.

What is claimed is:

1. A process for straightening or relaxing hair comprising:
   (a) providing a hair straightening/relaxing composition containing:
      (i) from about 0.1 to about 10% by weight of monoethanolamine;
      (ii) from about 1% to about 15% by weight of at least one protein denaturant selected from the group consisting of urea, urea derivatives and/or salts, guanidine salts chosen from guanidine hydrochloride and aminoguanidine hydrochloride, and mixtures thereof;
      (iii) remainder, to 100% by weight, a cosmetically acceptable medium, all weights based on the weight of the hair straightening/relaxing composition;
   (b) contacting the hair with the hair straightening/relaxing composition to form treated hair;
   (c) optionally, rinsing the hair straightening/relaxing composition from the treated hair;
   (d) optionally, contacting the treated hair with a non-volatile oil; and
   (e) smoothing the treated hair using a combination of heat and means for physically smoothing hair.

2. The process of claim 1 wherein (a) (i) is employed in an amount of from about 1 to about 10% by weight, based on the weight of the hair straightening/relaxing composition.

3. The process of claim 1 wherein (a) (i) has a pKa of from about 0 to about 15.

4. The process of claim 1 wherein (b) is performed for less than about 60 minutes.

5. The process of claim 1 wherein (b) is performed for less than about 20 minutes.

6. The process of claim 1 wherein the process is performed without the use of a barrier substance.

7. The process of claim 1 wherein (d) is chosen from plant, mineral, animal and synthetic oils.

8. The process of claim 1 wherein the heat employed in step (e) is at least about 50° C.

9. The process of claim 1 wherein the heat employed in step (e) is at least about 100° C.

10. The process of claim 1 wherein the means for physically smoothing hair is chosen from a brush and a comb.

11. The process of claim 1 wherein step (e) is performed using a hot/flat iron at a temperature of at least about 100° C.

12. A composition for treating hair comprising:
   (a) from about 0.1 to about 10% by weight of monoethanolamine;
   (b) from about 1% to about 15% by weight of at least one protein denaturant selected from the group consisting of urea, urea derivatives and/or salts, guanidine salts chosen from guanidine hydrochloride and aminoguanidine hydrochloride, and mixtures thereof; and
   (c) remainder, to 100% by weight, a cosmetically acceptable medium, all weights based on the weight of the hair straightening/relaxing composition.

13. The process of claim 1, wherein (a) (ii) is urea, present in an amount of from about 10 to about 15% by weight, based on the weight of the hair straightening/relaxing composition.

14. The composition of claim 12, wherein the guanidine salt is present in an amount of from about 1 to about 3% by weight, based on the weight of the hair straightening/relaxing composition.

15. The composition of claim 12, wherein (b) is urea, present in an amount of from about 10 to about 15% by weight, based on the weight of the hair straightening/relaxing composition.

16. The process of claim 1, wherein the guanidine salt is present in an amount of from about 1 to about 3% by weight, based on the weight of the hair straightening/relaxing composition.

* * * * *